United States Patent
Bough

(10) Patent No.: US 10,005,707 B2
(45) Date of Patent: Jun. 26, 2018

(54) TREATMENT OF ALCOHOL COMPOSITIONS

(71) Applicant: BP p.l.c., London (GB)

(72) Inventor: Matthew Bough, Middlesex (GB)

(73) Assignee: BP P.L.C., London (GB)

( * ) Notice: Subject to any disclaimer, the term of this patent is extended or adjusted under 35 U.S.C. 154(b) by 0 days. days.

(21) Appl. No.: 15/107,674

(22) PCT Filed: Dec. 19, 2014

(86) PCT No.: PCT/EP2014/078713
§ 371 (c)(1),
(2) Date: Jun. 23, 2016

(87) PCT Pub. No.: WO2015/097082
PCT Pub. Date: Jul. 2, 2015

(65) Prior Publication Data
US 2016/0326076 A1 Nov. 10, 2016

(30) Foreign Application Priority Data

Dec. 24, 2013 (EP) .................................... 13199525

(51) Int. Cl.
*C07C 29/80* (2006.01)
*C10L 1/02* (2006.01)
(Continued)

(52) U.S. Cl.
CPC .............. *C07C 29/80* (2013.01); *B01D 3/002* (2013.01); *B01D 3/143* (2013.01); *B01D 53/261* (2013.01);
(Continued)

(58) Field of Classification Search
USPC ......................................................... 44/627
See application file for complete search history.

(56) References Cited

U.S. PATENT DOCUMENTS

2012/0245395 A1    9/2012   Johnston et al.

FOREIGN PATENT DOCUMENTS

WO    WO 2009/048335 A1    4/2009
WO    WO 2009/063173 A1    5/2009
(Continued)

OTHER PUBLICATIONS

Lv, Huisheng, et al; "Removal of Acetic Acid from Fuel Ethanol Using Ion-Exchange Resin"; *Energy and Fuels*; vol. 26, pp. 7299-7307 (2012).
(Continued)

*Primary Examiner* — Ellen McAvoy
*Assistant Examiner* — Chantel Graham
(74) *Attorney, Agent, or Firm* — Nixon & Vanderhye P.C.

(57) ABSTRACT

Process for reducing the water and carboxylic acid content of an alcohol composition containing at least one $C_{1-4}$ alcohol, water and at least one $C_{1-4}$ carboxylic acid by (a) forming a vapor phase alcohol composition A and a liquid phase alcohol composition B, (b) separating a second vapor phase alcohol composition C and an aqueous phase D from the liquid phase alcohol composition B, the aqueous phase D containing the majority of the carboxylic acid that was present in the liquid phase alcohol composition B; (c) passing the vapor phase alcohol composition A to a drying unit, (d) passing the vapor phase alcohol composition C to a drying unit; and (e) recovering an alcohol composition from the drying units of steps (c) and (d). The recovered alcohol composition of step (e) has a reduced water and carboxylic acid content.

15 Claims, 5 Drawing Sheets

(51) Int. Cl.

| | | |
|---|---|---|
| *B01D 53/26* | (2006.01) | |
| *B01D 3/00* | (2006.01) | |
| *B01D 3/14* | (2006.01) | |
| *C07C 29/76* | (2006.01) | |
| *C07C 37/76* | (2006.01) | |
| *C07C 37/80* | (2006.01) | |

(52) U.S. Cl.
CPC .............. *C07C 29/76* (2013.01); *C07C 37/76* (2013.01); *C07C 37/80* (2013.01); *C10L 1/02* (2013.01); *C10L 2200/0469* (2013.01); *C10L 2290/06* (2013.01); *C10L 2290/10* (2013.01); *C10L 2290/12* (2013.01); *C10L 2290/543* (2013.01)

(56) References Cited

FOREIGN PATENT DOCUMENTS

| WO | WO 2009/063176 A1 | 5/2009 |
|---|---|---|
| WO | WO 2010/067079 A1 | 6/2010 |
| WO | WO 2012/062633 A1 | 5/2012 |

OTHER PUBLICATIONS

Lv, Huisheng, et al; "Removal of Acetic Acid from Fuel Ethanol Using Ion-Exchange Resin"; *Energy Fuels*; 26, 7299 (2012).

TREATMENT OF ALCOHOL COMPOSITIONS

This application is the U.S. national phase of International Application No. PCT/EP2014/078713 filed Dec. 19, 2014 which designated the U.S. and claims priority to European Patent Application No. 13199525.0 filed Dec. 24, 2013, the entire contents of each of which are hereby incorporated by reference.

BACKGROUND OF THE INVENTION

This invention provides a process for the reduction of water and carboxylic acid content of an alcohol composition. Also provided is a process for the preparation of a fuel ethanol composition from an ethanol composition comprising water and acetic acid.

Alcohols and other oxygenate compounds are being increasingly used in gasoline compositions for many reasons. Ethanol in particular is being increasingly used in gasoline, and in many jurisdictions the regular grade gasoline available through retail channels contains ethanol.

Alcohols may be obtained through a variety of routes including: synthetic preparation, for example alcohols may be derived from synthesis gas, hydrogenation of carboxylic acids or esters, or by the hydration of alkenes; extraction from natural sources, such as natural fats and oils; and preparation by the fermentation of biomass.

In recent years, there has been considerable interest in the preparation of alcohols by fermentation processes; in particular, since ethanol may be used as a biofuel component in gasoline, there has been particular interest in the preparation of ethanol by the fermentation of biomass. The term "biomass" as used herein refers to any source of organic material from biological origin. Examples of fermentation processes include the direct fermentation of biomass, such as sources of a carbohydrate, to alcohol(s) as well as the fermentation of derivatives of biomass to alcohols. For instance, bioethanol may be obtained by fermentation of feedstocks derived from sugar cane, such as sugar cane molasses and sugar cane juice; sugar beet, such as sugar beet molasses and sugar beet juice; cereal crops, such as corn or wheat, and cereal crop derived feedstocks, such as corn syrup; and lignocellulosic materials, such as fast growing grasses or "energy grasses".

Alcohols may also be derived from a fermentation process performed on a feed stream comprising carbon monoxide and hydrogen, such as synthesis gas; such processes are referenced and described in WO 2012/062633 A1.

Alcohols may also be prepared via the hydrogenation of carboxylic acids and/or esters. For example WO 2009/063176 A1 discloses a process for the conversion of ethanoic acid into ethanol characterised by the following steps:
1. introducing ethanoic acid and $H_2$ into a primary hydrogenation unit in the presence of a precious metal-based catalyst to produce ethanol and ethyl ethanoate,
2. introducing ethyl ethanoate, from step 1, together with $H_2$, into a secondary hydrogenation unit in the presence of a copper-based catalyst to produce ethanol, and
3. recovering ethanol from step 2.

WO 2010/067079 A1 discloses a process for the preparation of alcohol(s) from alkyl ester(s) wherein hydrogen, carbon monoxide and at least one alkyl ester are brought into contact with a hydrogenation catalyst comprising copper and manganese in a reaction zone to produce at least one alcohol, wherein the molar ratio of hydrogen to carbon monoxide in the reaction zone is in the range of from 100:1 to 1:10.

WO 2009/063173 A1 discloses a process for the production of ethanol from ethanoic acid and $H_2$, characterised by the following steps:
1) introducing ethanoic acid, together with methanol and/or ethanol into an esterification reactor to produce methyl ethanoate and/or ethyl ethanoate,
2) introducing ethanoate from step 1, together with $H_2$, into a hydrogenation unit to produce a stream comprising ethanol, unreacted ethanoate and optionally methanol,
3) separating the resulting stream, from step 2, into unreacted ethanoate and ethanol and optionally methanol,
4) optionally reintroducing ethanoate, from step 3, into the esterification reactor of step 1,
5) using at least a part of the methanol and/or the ethanol of step 3, as the methanol and/or ethanol feed of the esterification reactor of step 1, and
6) recovering ethanol, from step 3.

Due to the requirements in the properties of gasoline, and in order to meet various gasoline specifications around the world, any alcohols or other oxygenate compounds that are to be used in gasoline compositions must be compatible with the base gasoline that it is blended with and must not introduce contaminants that would cause the thus formed gasoline to fail to meet the required properties or specifications. As such, it is necessary to control the levels of certain contaminants in alcohols and other oxygenates that are to be used in gasoline.

Due to the nature of alcohols, in particular the lower alcohols (having from one to four carbon atoms) and especially ethanol, water is often present in significant amounts as it tends to be miscible with lower alcohols and can frequently be difficult to remove, for example due to azeotropic behaviour of water and ethanol mixtures. Additionally, certain methods for the preparation of alcohols either use organic acids during the synthesis process or may lead to the production of trace amounts of organic acids as by-products. The presence of water and acids in gasoline is very strictly limited, and, consequently, the amount of water and acid in alcohol compositions that are to be blended in to gasoline would also be required to be limited.

The use of various desiccants for the drying of solvents, including alcohol compositions, is known in the art, including the use of certain molecular sieves. The use of molecular sieve 3A for the drying of ethanol is known in the art.

The removal of acetic acid from fuel ethanol using ion-exchange resins has been reported in 'Removal of Acetic Acid from Fuel Ethanol Using Ion-Exchange Resin' by Huisheng Lv, Yanpeng Sun, Mihua Zhang, Zhonfeng Geng and Miaomiao Ren in Energy Fuels, 26, 7299 (2012). In this article, ethanol compositions containing acetic acid were treated using basic ion-exchange resins in order to reduce the acidity of the composition.

Carboxylic acid may also be removed from alcohol compositions by distillation, for example acetic acid can be removed from ethanol in this way. However, heavier alcohols, which may also be present, and which are permissible impurities in fuel ethanol products, complicate the separation and, in general, any alcohol compositions produced by distillation will need to be dried. Additionally, distillation requires relatively large amounts of energy, leading to significantly increased costs. It would therefore be advantageous to limit the amount of distillation required when separating acids from alcohol compositions.

SUMMARY OF THE INVENTION

There exists a need in the art for a process which can reduce both the amount of water and the acidity in alcohol compositions, such as alcohol compositions for use in fuels.

The present invention provides a process for reducing the water and carboxylic acid content of an alcohol composition comprising at least one alcohol having from one to four carbon atoms, water and at least one carboxylic acid having from one to four carbon atoms, wherein said process comprises:

(a) forming a vapour phase alcohol composition A and a liquid phase alcohol composition B from the alcohol composition;

(b) separating a second vapour phase alcohol composition C and an aqueous phase D from the liquid phase alcohol composition B in a distillation column, wherein the aqueous phase D contains the majority of the carboxylic acid that was present in the liquid phase alcohol composition B;

(c) passing the vapour phase alcohol composition A to a drying unit comprising a desiccant;

(d) passing the vapour phase alcohol composition C to a drying unit comprising a desiccant; and (e) recovering an alcohol composition from the drying unit of step (c) and the drying unit of step (d);

wherein the recovered alcohol composition of step (e) has a reduced water and carboxylic acid content.

The present invention also provides a process for reducing the water and acetic acid content of an ethanol composition comprising ethanol, water and acetic acid, wherein said process comprises:

(a) forming a vapour phase ethanol composition A and a liquid phase ethanol composition B from the ethanol composition;

(b) separating a second vapour phase ethanol composition C and an aqueous phase D from the liquid phase ethanol composition B in a distillation column, wherein the aqueous phase D contains the majority of the acetic acid that was present in the liquid phase ethanol composition B;

(c) passing the vapour phase ethanol composition A to a drying unit comprising a desiccant;

(d) passing the vapour phase ethanol composition C to a drying unit comprising a desiccant; and (e) recovering an ethanol composition from the drying unit of step (c) and the drying unit of step (d);

wherein the recovered ethanol composition of step (e) has a reduced water and acetic acid content.

The present invention also provides a process for the preparation of a fuel ethanol composition suitable for use in ethanol-containing gasoline compositions from an ethanol composition comprising ethanol, water and acetic acid, wherein said process comprises:

(a) forming a vapour phase ethanol composition A and a liquid phase ethanol composition B from the ethanol composition;

(b) separating a second vapour phase ethanol composition C and an aqueous phase D from the liquid phase ethanol composition B in a distillation column, wherein the aqueous phase D contains the majority of the acetic acid that was present in the liquid phase ethanol composition B;

(c) passing the vapour phase ethanol composition A to a drying unit comprising a desiccant;

(d) passing the vapour phase ethanol composition C to a drying unit comprising a desiccant; and (e) recovering a fuel ethanol composition from the drying unit of step (c) and the drying unit of step (d);

wherein the recovered fuel ethanol composition of step (e) has a reduced water and acetic acid content.

The present invention also provides a process for reducing the water and butyric acid content of a butanol composition comprising at least one butanol, water and butyric acid, wherein said process comprises:

(a) forming a vapour phase butanol composition A and a liquid phase butanol composition B from the butanol composition;

(b) separating a second vapour phase butanol composition C and an aqueous phase D from the liquid phase butanol composition B in a distillation column, wherein the aqueous phase D contains the majority of the butyric acid that was present in the liquid phase butanol composition B;

(c) passing the vapour phase butanol composition A to a drying unit comprising a desiccant;

(d) passing the vapour phase butanol composition C to a drying unit comprising a desiccant; and (e) recovering a butanol composition from the drying unit of step (c) and the drying unit of step (d);

wherein the recovered fuel butanol composition of step (e) has a reduced water and butyric acid content.

The present invention also provides a process for the preparation of a fuel butanol composition suitable for use in butanol-containing gasoline compositions from a butanol composition comprising at least one butanol, water and butyric acid, wherein said process comprises:

(a) forming a vapour phase butanol composition A and a liquid phase butanol composition B from the butanol composition;

(b) separating a second vapour phase butanol composition C and an aqueous phase D from the liquid phase butanol composition B in a distillation column, wherein the aqueous phase D contains the majority of the butyric acid that was present in the liquid phase butanol composition B;

(c) passing the vapour phase butanol composition A to a drying unit comprising a desiccant;

(d) passing the vapour phase butanol composition C to a drying unit comprising a desiccant; and (e) recovering a fuel butanol composition from the drying unit of step (c) and the drying unit of step (d);

wherein the recovered fuel butanol composition of step (e) has a reduced water and butyric acid content.

The process of the present invention comprises the step of forming a vapour phase alcohol composition A and a liquid phase alcohol composition B from the alcohol composition comprising at least one alcohol having from one to four carbon atoms, water and at least one carboxylic acid having from one to four carbon atoms. This step may be carried out using any suitable method. However, in a particular embodiment, the vapour phase alcohol composition A and the liquid phase alcohol composition B are formed by vaporisation of the alcohol composition, for example by passing all of the alcohol composition to a vaporisation unit configured to divide the alcohol composition into a vapour phase alcohol composition A and a liquid phase alcohol composition B.

In an alternative embodiment, the vapour phase alcohol composition A and the liquid phase alcohol composition B are formed by dividing the alcohol composition into a first portion and a second portion, passing the first portion to a vaporisation unit, so that substantially all of the first portion is vaporised in the vaporisation unit to form the vapour phase alcohol composition A, and passing the second portion to the distillation column as the liquid phase alcohol composition B.

In a further alternative embodiment, the vapour phase alcohol composition A and the liquid phase alcohol composition B are formed by pre-dividing the alcohol composition into a first portion and a second portion, passing the first portion to a vaporisation unit, so that the first portion is divided in the vaporisation unit into the vapour phase alcohol composition A and a third portion, and passing the second portion and the third portion to the distillation column as the liquid phase alcohol composition B. In this embodiment, the second and the third portion may be passed separately to the distillation column, or they may be combined before being passed to the distillation column.

In embodiments of the present invention in which the vapour phase alcohol composition A is formed by vaporisation, any suitable vaporisation conditions may be used. The conditions used will also depend upon whether all of the feed to the vaporisation step is to be converted to the vapour phase alcohol composition A, or only part of the feed is to be converted to the vapour phase alcohol composition A and part is to be maintained as a liquid phase.

Depending upon the vaporisation conditions used, the vaporisation step may result in the vapour phase alcohol composition A and the liquid phase alcohol composition B having different compositions; however, preferably, the vaporisation step does not result in a significant difference in the concentration of water present in the vapour phase alcohol composition A and the liquid phase alcohol composition B. More preferably, the vaporisation step B does not result in a significant difference in the concentration of water and carboxylic acid present in the vapour phase alcohol composition and the concentrations of these components in the liquid phase alcohol composition B.

In embodiments of the present invention in which the alcohol composition comprising at least one alcohol having from one to four carbon atoms, water and at least one carboxylic acid having from one to four carbon atoms is pre-divided into a first portion and a second portion, any suitable method of pre-dividing the alcohol composition may be used, such as simple volumetric division of the alcohol composition by, for example, flow control.

In the process of the present invention, the proportion of the alcohol composition comprising at least one alcohol having from one to four carbon atoms, water and at least one carboxylic acid having from one to four carbon atoms forming the vapour phase alcohol composition A, and the resulting proportion forming the liquid phase alcohol composition B, may vary from substantially all of the alcohol composition forming the vapour phase alcohol composition A, with substantially none forming the liquid phase alcohol composition B, to substantially all of the alcohol composition forming the liquid phase alcohol composition B, with substantially none of the alcohol composition forming the vapour phase alcohol composition A. Preferably however, the proportion of the alcohol composition forming the vapour phase alcohol composition A and the proportion forming the liquid phase alcohol composition B is set so that the acid level in the final product meets the required specification. Preferably, from 1 to 99% of the alcohol composition may form the vapour phase alcohol composition A, more preferably from 5 to 95% of the alcohol composition may form the vapour phase alcohol composition A, more preferably from 10 to 90% of the alcohol composition may form the vapour phase alcohol composition A, and most preferably from 25 to 75% of the alcohol composition may form the vapour phase alcohol composition A; with, in each case, the remaining proportion of the alcohol composition forming the liquid phase alcohol composition B.

The process of the present invention comprises separating a second vapour phase alcohol composition C and an aqueous phase D from the liquid phase alcohol composition B in a distillation column, wherein the aqueous phase D contains the majority of the carboxylic acid that was present in the liquid phase alcohol composition B. Any suitable condition may be used in the distillation column to separate the second vapour phase alcohol composition C and the aqueous phase D from the liquid phase alcohol composition B.

The process of the present invention comprises passing the vapour phase alcohol composition A to a drying unit comprising a desiccant and passing the vapour phase alcohol composition C to a drying unit comprising a desiccant. The vapour phase alcohol composition A and the vapour phase alcohol composition C may be passed to different drying units. However, in a preferred embodiment, the vapour phase alcohol composition A and the vapour phase composition C are passed to the same drying unit comprising a desiccant.

In embodiments of the present invention in which the vapour phase alcohol composition A and the vapour phase alcohol composition C are passed to the same drying unit comprising a desiccant, the vapour phase alcohol composition A and the vapour phase alcohol composition C may be passed separately to the drying unit comprising a desiccant; however, in a preferred embodiment, the vapour phase alcohol composition A and the vapour phase alcohol composition C are combined prior to being passed to the drying unit comprising a desiccant.

The process of the present invention comprises recovering an alcohol composition from the drying unit of step (c) and the drying unit of step (d). Where the vapour phase alcohol composition A and the vapour phase alcohol composition C are dried in the same drying unit comprising a desiccant and are mixed therein, for example either by being combined prior to being passed to the drying unit comprising a desiccant or by being supplied to the drying unit comprising a desiccant at substantially the same time, the step of recovering the alcohol composition merely comprises removing the dried product stream from the drying unit comprising a desiccant. Where the vapour phase alcohol composition A and the vapour phase alcohol composition C are dried in separate drying units comprising a desiccant, or where they are dried in the same drying unit comprising a desiccant but are supplied thereto at different times, the step of recovering the alcohol composition will comprise recovering the separate dried streams and combining them to form the alcohol composition. The recovered alcohol composition obtained from the single drying unit when only one drying unit is used, or the recovered alcohol composition obtained by combining the effluent from two or more drying units, has a reduced water and carboxylic acid content in comparison to the alcohol composition to be treated in the process.

The alcohol composition to be treated in the process of the present invention comprises at least one alcohol having one to four carbon atoms, water and at least one carboxylic acid having from one to four carbon atoms. Preferably, the alcohol composition to be treated in the process of the present invention comprises at least one alcohol having two to four carbon atoms, water and at least one carboxylic acid having from two to four carbon atoms.

In one particular embodiment of the present invention, the alcohol composition to be treated comprises at least 90 wt % alcohol(s), preferably the alcohol composition comprises at least 93 wt % alcohol(s), more preferably the alcohol composition comprises at least 95 wt % alcohol(s).

In one particular embodiment of the present invention, the alcohol composition to be treated in the process of the present invention comprises ethanol, water and at least one carboxylic acid having from one to four carbon atoms.

In a specific embodiment wherein the alcohol composition to be treated in the process of the present invention comprises ethanol, the alcohol composition comprises a greater amount of ethanol (on a weight basis) than the total amount of other alcohols present in the alcohol composition. Therefore, in this embodiment, the alcohol composition to be treated in the process of the present invention is an ethanol composition comprising ethanol, water and at least one carboxylic acid having from one to four carbon atoms; optionally the ethanol composition may contain one or more other alcohols, in particular, selected from methanol, propanol(s) and butanol(s).

In the embodiment wherein the alcohol composition to be treated is an ethanol composition, said ethanol composition may also contain other alcohols, however, preferably at least 85 wt % of the alcohols present in the alcohol composition is ethanol, more preferably at least 90 wt % of the alcohols present in the alcohol composition is ethanol, even more preferably at least 95 wt % of the alcohols present in the alcohol composition is ethanol.

In one particular embodiment, the alcohol composition to be treated in the process of the present invention is an ethanol composition comprising ethanol, water and at least one carboxylic acid having from one to four carbon atoms, wherein said ethanol composition comprises at least 90 vol % ethanol, preferably at least 93 vol % ethanol, more preferably at least 95 vol % ethanol, such as 95.6 vol % ethanol, based on the total ethanol composition. In one specific embodiment of the present invention wherein the alcohol composition to be treated is an ethanol composition, said ethanol composition comprises an amount of water and an amount of the carboxylic acid which cannot be further reduced by distillation.

In another particular embodiment of the present invention, the alcohol composition to be treated in the process of the present invention comprises at least one butanol, water and at least one carboxylic acid having from one to four carbon atoms.

In a specific embodiment wherein the alcohol composition to be treated in the process of the present invention comprises at least one butanol, the alcohol composition comprises a greater amount of butanol(s) (on a weight basis) than the total amount of other alcohols present in the alcohol composition. Therefore, in this embodiment, the alcohol composition to be treated in the process of the present invention is a butanol composition comprising at least one butanol, water and at least one carboxylic acid having from one to four carbon atoms; optionally the butanol composition may contain one or more other alcohols.

In the embodiment wherein the alcohol composition to be treated is a butanol composition, said butanol composition may also contain other alcohols, however, preferably at least 85 wt % of the alcohols present in the butanol composition is butanol(s), more preferably at least 90 wt % of the alcohols present in the butanol composition is butanol(s), even more preferably at least 95 wt % of the alcohols present in the butanol composition is butanol(s).

In one particular embodiment, the alcohol composition to be treated in the process of the present invention is a butanol composition comprising water and at least one carboxylic acid having from one to four carbon atoms, wherein said butanol composition comprises at least 90 vol % butanol, preferably at least 93 vol % butanol, more preferably at least 95 vol % butanol, based on the total alcohol composition. In one specific embodiment of the present invention wherein the alcohol composition to be treated is a butanol composition, said butanol composition comprises an amount of water and an amount of the carboxylic acid which cannot be further reduced by distillation.

In one particular embodiment of the present invention, the alcohol composition to be treated comprises at most 5 wt % carboxylic acid(s), preferably at most 1 wt % carboxylic acid(s), more preferably at most 0.5 wt % carboxylic acid(s), and typically at most 0.25 wt % carboxylic acid(s); independently of the maximum stated amounts of carboxylic acid(s) in this embodiment, the alcohol composition to be treated comprises at least 25 ppm by weight carboxylic acid(s), preferably at least 50 ppm by weight carboxylic acid(s), more preferably at least 100 ppm by weight carboxylic acid(s), even more preferably at least 250 ppm by weight carboxylic acid(s), and typically at least 500 ppm by weight carboxylic acid(s).

In one particular embodiment of the present invention, the alcohol composition to be treated in the process of the present invention is an alcohol composition comprising at least one alcohol having one to four carbon atoms, water and acetic acid. In the embodiment wherein the alcohol composition to be treated comprises acetic acid, said alcohol composition may also contain other carboxylic acids.

In the embodiment wherein the alcohol composition to be treated in the process of the present invention comprises acetic acid, said alcohol composition may also contain other carboxylic acids, however, preferably at least 85 wt % of the carboxylic acids present in the alcohol composition is acetic acid, more preferably at least 90 wt % of the carboxylic acids present in the alcohol composition is acetic acid, even more preferably at least 95 wt % of the carboxylic acids present in the alcohol composition is acetic acid.

In one particular embodiment of the present invention, the alcohol composition to be treated in the process of the present invention is an ethanol composition comprising ethanol, water and acetic acid, said ethanol composition may also contain other alcohols and/or carboxylic acids. Preferred amounts of ethanol and acetic acid present in such an ethanol composition are the same as the preferred amounts independently stated in relation to ethanol compositions and compositions comprising acetic acid.

In another particular embodiment of the present invention, the alcohol composition to be treated in the process of the present invention is an alcohol composition comprising at least one alcohol having one to four carbon atoms, water and butyric acid. In the embodiment wherein the alcohol composition to be treated comprises butyric acid, said alcohol composition may also contain other carboxylic acids.

In the embodiment wherein the alcohol composition to be treated in the process of the present invention comprises butyric acid, said alcohol composition may also contain other carboxylic acids, however, preferably at least 85 wt % of the carboxylic acids present in the alcohol composition is butyric acid, more preferably at least 90 wt % of the carboxylic acids present in the alcohol composition is butyric acid, even more preferably at least 95 wt % of the carboxylic acids present in the alcohol composition is butyric acid.

In one particular embodiment of the present invention, the alcohol composition to be treated is a butanol composition comprising at least one butanol, water and butyric acid, said butanol composition may also contain other alcohols and/or carboxylic acids. Preferred amounts of butanol(s) and butyric acid present in such a butanol composition are the same as the preferred amounts independently stated in relation to butanol compositions and compositions comprising butyric acid.

In one particular embodiment of the present invention, the alcohol composition to be treated comprises at most 10 wt % water, preferably the alcohol composition comprises at most 7 wt % water, more preferably the alcohol composition comprises at most 5 wt % water; independently of the maximum stated amounts of water in this embodiment, the alcohol composition to be treated comprises at least 100 ppm by weight water, preferably at least 250 ppm by weight water, more preferably at least 500 ppm by weight water, and typically at least 1000 ppm by weight water.

In the process of the present invention, the vapour phase alcohol composition A and the vapour phase alcohol composition C are both passed to drying units comprising a desiccant, and these may be the same or different drying units. Any suitable desiccant may be incorporated in the drying unit(s) used in the process of the present invention. Suitable desiccant materials include porous and inorganic oxide material(s), molecular sieves, sodium sulphate, potassium carbonate, silica gels and cellulose material(s), such as cornmeal, straw and sawdust. Where more than one drying unit is present, the drying units may comprise the same or different desiccant materials.

In a particular embodiment of the present invention, the desiccant comprise at least one porous inorganic oxide material, preferably wherein at least one of the porous inorganic oxide material(s) contains Brønsted acid sites and/or neutralised Brønsted acid sites.

In one particular embodiment of the present invention, the majority of the Brønsted acid sites in the porous inorganic oxide material(s) are neutralised Brønsted acid sites. In yet another particular embodiment of the present invention, essentially all of the Brønsted acid sites in the porous inorganic oxide material(s) are neutralised Brønsted acid sites. Neutralisation of Brønsted acid sites in porous inorganic materials is well known in the art and may be achieved through a variety of known techniques, such as ion exchange of the protons on the Brønsted acid sites with metal cations. Preferred metal cations that can be used as the counter ion on the neutralised Brønsted acid sites in the porous inorganic material(s) in the present invention are selected from the cations of the alkali metals; more preferably selected from the cations of lithium, sodium, potassium and mixtures thereof; even more preferably selected from the cations of sodium, potassium and mixtures thereof; most preferably selected from the cations of sodium and potassium.

The desiccant(s) in the drying unit(s) used in the process of the present invention will typically be in the form of one or more beds of solid particulate material.

The desiccant bed may optionally comprise other materials in addition to the porous inorganic oxide material.

In one embodiment of the present invention, the desiccant bed is an admixture of a desiccant material and a porous inorganic oxide material containing Brønsted acid sites and/or neutralised Brønsted acid sites, wherein said porous inorganic oxide material containing Brønsted acid sites and/or neutralised Brønsted acid sites is different to the desiccant material. In this embodiment of the present invention, the desiccant material which is admixed with the porous inorganic oxide material may be any material which is useful as a desiccant in the drying of the alcohol composition to be treated in the present invention.

In another embodiment of the present invention, the desiccant bed consists of one or more porous inorganic oxide materials containing Brønsted acid sites and/or neutralised Brønsted acid sites, wherein one or more of said porous inorganic materials function as a desiccant when used in the alcohol composition to be treated in the present invention.

By the term "function as a desiccant" it is meant that the porous inorganic oxide material(s) would absorb and/or adsorb water in the alcohol composition under process conditions.

In a preferred embodiment of the present invention, the porous inorganic oxide material is a porous inorganic oxide material comprising pores having a pore aperture of a size that would allow water to enter preferentially over the alcohols present in the alcohol composition; i.e. the pore aperture being of a size sufficiently large so as to allow water molecules to readily enter the pore, but sufficiently small so as to make it the pores less readily accessible to the alcohols present in the alcohol composition. The selection of the maximum pore size would be dependent upon the alcohols present in the alcohol composition.

In a more preferred embodiment of the present invention, the porous inorganic oxide material is a porous inorganic oxide material comprising pores having a pore aperture in the range of from 2.5 to 4.5 Å (0.25 to 0.45 nm).

In one particular embodiment, the porous inorganic oxide material is at least one oxide of silicon, aluminum and mixtures thereof, preferably, the porous inorganic oxide material is an alumina-silicate; in a specific aspect of this embodiment, the porous inorganic oxide material comprises an alkali metal alumina-silicate, preferably the porous inorganic oxide material is an alkali metal alumina-silicate, more preferably selected from a potassium alumina-silicate, sodium alumina-silicate and mixtures thereof. In one particular embodiment of the present invention, the porous inorganic oxide material comprises at least one zeolite, more particularly, the porous inorganic oxide material comprises at least one material having a zeolite A framework.

In one particular embodiment of the present invention, the porous inorganic oxide material comprises a molecular sieve material, preferably selected from molecular sieve 3A, molecular sieve 4A and mixtures thereof.

Molecular sieve 3A (also referred to herein as 3 Å molecular sieve) is a molecular sieve having an effective pore opening of approximately 3 Å (0.3 nm) in diameter and is known in the art and are commercially available. Typically, molecular sieve 3A is a potassium form of the type "A" zeolite crystal structure, having a typical formula: $2/3K_2O.1/3Na_2O\text{—}Al_2O_3.2SiO_2.9/2\ H_2O$ and a silica to alumina (SAR) ratio of approximately 2:1.

Molecular sieve 4A (also referred to herein as 4 Å molecular sieve) is a molecular sieve having an effective pore opening of approximately 4 Å (0.4 nm) in diameter and is known in the art and are commercially available. Typically, molecular sieve 4A is a sodium form of the type "A" zeolite crystal structure, having a typical formula: $Na_2O\text{—}Al_2O_3.2SiO_2.9/2H_2O$ and a silica to alumina (SAR) ratio of approximately 2:1.

Both molecular sieve 3A and molecular sieve 4A are known to function as desiccants.

In one specific embodiment of the present invention, the porous inorganic oxide material comprises molecular sieve 3A; preferably, in this embodiment the porous inorganic oxide material is molecular sieve 3A.

In another specific embodiment of the present invention, the porous inorganic oxide material comprises molecular sieve 4A; preferably, in this embodiment the porous inorganic oxide material is molecular sieve 4A.

In one specific embodiment of the present invention, the desiccant bed consists of a porous inorganic oxide material selected from molecular sieve 3A, molecular sieve 4A and mixtures thereof.

The porous inorganic oxide material may comprise a binder material in addition to a porous inorganic oxide component. In the embodiments wherein the porous inorganic oxide material comprises a binder material, the binder material may be selected from any suitable binder material.

In the embodiments wherein the porous inorganic oxide material comprises a binder material, the binder material is preferably a refractory inorganic oxide such that the inorganic oxide is stable at high temperature, such as a temperature of at least 400° C., for example, a temperature in the range 400 to 550° C. In a preferred aspect of this embodiment of the present invention, the binder material is selected from at least one of the group of silicas, aluminas, silica-aluminas, titanias, magnesium silicates and magnesium aluminium silicates. Aluminas or silica-aluminas are particularly useful. Examples of suitable aluminas include boehmite type alumina and gamma alumina. Where a silica-alumina is used, its silica content is preferably in the range 5 to 40 wt %, suitably in the range 5 to 10 wt %. Preferably, the silica-alumina is amorphous.

In the embodiments wherein the porous inorganic oxide material comprises a binder material, the porosity of the binder material is preferably no greater than the porosity of the porous inorganic oxide component; in a particularly preferred aspect of the present invention, the binder material does not contain pores having a pore diameter greater than the pore diameter of the pores contained in the porous inorganic oxide component.

In the embodiments wherein the porous inorganic oxide material comprises a binder material, the amount of binder material present in the porous inorganic oxide material is preferably in the range of from 10 to 80 wt % and more preferably in the range of from 20 to 60 wt %.

In the embodiments wherein the porous inorganic oxide material comprises a binder material and a porous inorganic oxide component, the porous inorganic oxide component may be selected from inorganic oxide materials comprising pores having a pore aperture of a size that would allow water to enter preferentially over the alcohols present in the alcohol composition, as described above. Examples of suitable porous inorganic oxide components are porous inorganic oxide compounds having a pore aperture in the range of from 2.5 to 4.5 Å (0.25 to 0.45 nm); specific examples of suitable porous inorganic oxide components are molecular sieve materials, preferably selected from molecular sieve 3A, molecular sieve 4A and mixtures thereof.

In one specific embodiment wherein the porous inorganic oxide material comprises a binder material, the porous inorganic oxide component functions as a desiccant and the binder material comprises Brønsted acid sites and/or neutralised Brønsted acid sites. In such embodiments, the porous inorganic oxide component thereof will preferably also contain Brønsted acid sites and/or the neutralised Brønsted acid sites.

In another specific embodiment wherein the porous inorganic oxide material comprises a binder material, the porous inorganic oxide component comprises Brønsted acid sites and/or neutralised Brønsted acid sites and the binder material functions as a desiccant. In such embodiments, the porous inorganic oxide component thereof may also function as a desiccant and the binder material may also contain Brønsted acid sites and/or the neutralised Brønsted acid sites.

In the process of the present invention, the vapour phase alcohol composition A and the vapour phase alcohol composition C are preferably dried in the respective drying units comprising a desiccant by being brought into contact with a desiccant bed at elevated temperature. By the term "elevated temperature", it is meant a temperature which is greater than the ambient temperature.

Preferably, the temperature at which the vapour phase alcohol composition A and/or C is brought in to contact with the desiccant bed is a temperature of at least 70° C., more preferably at least 90° C., more preferably at least 110° C., even more preferably at least 120° C., and even more preferably at least 130° C., for example at least 140° C.

In specific embodiments of the present invention, the temperature at which the vapour phase alcohol composition A and/or C is brought in to contact with the desiccant bed is a temperature in a range defined by a combination of a lower temperature limit selected from 70° C., 90° C., 110° C., 120° C., 130° C., and 140° C., and an upper temperature limit selected from 250° C., 230° C., 220° C., 210° C., 200° C., and 190° C. (i.e. a temperature range selected from: 70° C. to 250° C.; 70° C. to 230° C.; 70° C. to 220° C.; 70° C. to 210° C.; 70° C. to 200° C.; 70° C. to 190° C.; 90° C. to 250° C.; 90° C. to 230° C.; 90° C. to 220° C.; 90° C. to 210° C.; 90° C. to 200° C.; 90° C. to 190° C.; 110° C. to 250° C.; 110° C. to 230° C.; 110° C. to 220° C.; 110° C. to 210° C.; 110° C. to 200° C.; 110° C. to 190° C.; 120° C. to 250° C.; 120° C. to 230° C.; 120° C. to 220° C.; 120° C. to 210° C.; 120° C. to 200° C.; 120° C. to 190° C.; 130° C. to 250° C.; 130° C. to 230° C.; 130° C. to 220° C.; 130° C. to 210° C.; 130° C. to 200° C.; 130° C. to 190° C.; 140° C. to 250° C.; 140° C. to 230° C.; 140° C. to 220° C.; 140° C. to 210° C.; 140° C. to 200° C.; and, 140° C. to 190° C.).

The pressure at which the vapour phase alcohol composition A and/or C is brought in to contact with the desiccant bed is a pressure of at least 0.15 MPa, more preferably at least 0.2 MPa, more preferably at least 0.3 MPa, even more preferably at least 0.4 MPa, and even more preferably at least 0.5 MPa.

In specific embodiments of the process of the present invention wherein the vapour phase alcohol composition A and/or C is brought in to contact with the desiccant bed, the pressure at which the vapour phase alcohol composition A and/or C is brought in to contact with the desiccant bed is a pressure in a range defined by a combination of a lower pressure limit selected from 0.15 MPa, 0.2 MPa, 0.3 MPa, 0.4 MPa, and 0.5 MPa, and an upper pressure limit selected from 5 MPa, 4 MPa, 3 MPa, 2 MPa and 1 MPa (i.e. a pressure range selected from: 0.15 MPa to 5 MPa; 0.15 MPa to 4 MPa; 0.15 MPa to 3 MPa; 0.15 MPa to 2 MPa; 0.15 MPa to 1 MPa; 0.2 MPa to 5 MPa; 0.2 MPa to 4 MPa; 0.2 MPa to 3 MPa; 0.2 MPa to 2 MPa; 0.2 MPa to 1 MPa; 0.3 MPa to 5 MPa; 0.3 MPa to 4 MPa; 0.3 MPa to 3 MPa; 0.3 MPa to 2 MPa; 0.3 MPa to 1 MPa; 0.4 MPa to 5 MPa; 0.4 MPa to 4 MPa; 0.4 MPa to 3 MPa; 0.4 MPa to 2 MPa; 0.4 MPa to 1 MPa; 0.5 MPa to 5 MPa; 0.5 MPa to 4 MPa; 0.5 MPa to 3 MPa; 0.5 MPa to 2 MPa; and, 0.5 MPa to 1 MPa).

Conveniently, the vapour phase alcohol composition A and/or C is brought in to contact with the porous inorganic oxide material by passing the vapour phase alcohol composition A and/or C through one or more desiccant beds comprising the porous inorganic oxide material. Any configuration of system which brings the vapour phase composition A and/or C in to contact with a bed of solid material may be employed.

In one particular embodiment of the process of the present invention, the, or each, drying unit comprises a single desiccant bed, wherein the vapour phase alcohol composition A and/or C is brought in to contact with the desiccant bed by passing the vapour phase alcohol composition through said single desiccant bed.

In another particular embodiment of the process of the present invention, the, or each, drying unit comprises two or more sequential desiccant beds. In this embodiment, the vapour phase alcohol composition A and/or C is brought in to contact with the desiccant bed by passing the vapour phase alcohol composition through two or more desiccant beds arranged sequentially, wherein the effluent from a first desiccant bed is passed through a second desiccant bed; optionally, the effluent from the second desiccant bed is passed through one or more subsequent desiccant beds.

The use of sequential beds would enable the use of different desiccant beds so that the adsorption of the water may be optimised.

In one particular embodiment of the process of the present invention, the, or each, drying unit comprises two or more parallel desiccant beds. By the term "parallel beds" used herein, configurations comprising both traditional parallel beds as well as configurations comprising two or more beds which are not arranged in series and operate independently of each other, allowing the switching of the feed from one bed to the other (e.g. 'pressure swing' and 'temperature swing' systems), are encompassed by this term. In this embodiment, it is possible to contact the vapour phase alcohol composition A and/or C with the desiccant in at least one of the desiccant beds (the 'active bed(s)') whilst at least one of the other, parallel, desiccant beds is being regenerated (the 'regenerating bed(s)'). Operation of such systems would enable regeneration of the desiccant beds during operation of the process of the present invention through the use of systematic changing of the active and regenerating beds, such systematic changing of the active and regenerating beds may be automated or may be manually controlled, and the switching of the active and regenerating beds may be performed upon a predetermined schedule or may be performed through monitoring of the performance of the desiccant bed(s) through monitoring of the effluent stream from the active bed(s) and/or the regenerating bed(s).

In another embodiment of the process of the present invention, the, or each, drying unit comprises two or more parallel desiccant beds and at least one desiccant bed which is sequentially arranged with one or more of the parallel beds.

The desiccant bed, or beds, with which the vapour phase alcohol composition A and/or C is contacted will adsorb water, and, due to the increasing saturation of the desiccant bed, will reduce in efficiency as a desiccant over time. When sufficient reduction in efficiency as a desiccant occurs, the desiccant bed may either be replaced or regenerated; preferably, the desiccant bed is regenerated.

The determination of when to replace or regenerate the desiccant bed will depend on many factors, such as the maximum amount of water and/or acid acceptable in the effluent alcohol composition, which would vary depending upon the intended use of the alcohol composition.

BRIEF DESCRIPTION OF THE DRAWINGS

The regeneration of the desiccant bed, or beds, can be performed by any means known in the art for the regeneration of a desiccant material. Typically, the regeneration of the desiccant bed may be performed by contacting the desiccant bed with a carrier fluid containing essentially no water and either increasing the temperature of the desiccant to a temperature at which the water is desorbed from the desiccant bed into the carrier fluid or reducing the pressure to a pressure at which the water is desorbed from the desiccant bed into the carrier fluid; whilst the regeneration of the desiccant bed via means of increasing the temperature may be performed in both the liquid and the vapour phase, the regeneration of the desiccant bed via means of decreasing the pressure would be performed in the vapour phase only. A particularly convenient carrier fluid (either liquid phase or gas phase) which may be used for the regeneration of the desiccant bed is the dried alcohol which is effluent from the process of the present invention; alternative carrier fluids include other dry alcohols (either in the gas phase or liquid phase), dry alkanes (either in the gas phase or liquid phase), or gases which are inert in the desiccant bed, such as dry nitrogen and dry carbon dioxide.

In a particular embodiment, the process of the present invention further comprises using a portion of the alcohol composition having reduced a water and carboxylic content recovered in step (e) to regenerate the drying unit of step (c) and/or step (d). Optionally in this embodiment, the process further comprises passing a portion of the resulting stream comprising alcohol and water to the distillation column for distillation, together with the liquid phase alcohol composition B, to form the second vapour phase alcohol composition C and the aqueous phase D.

Figure 1:
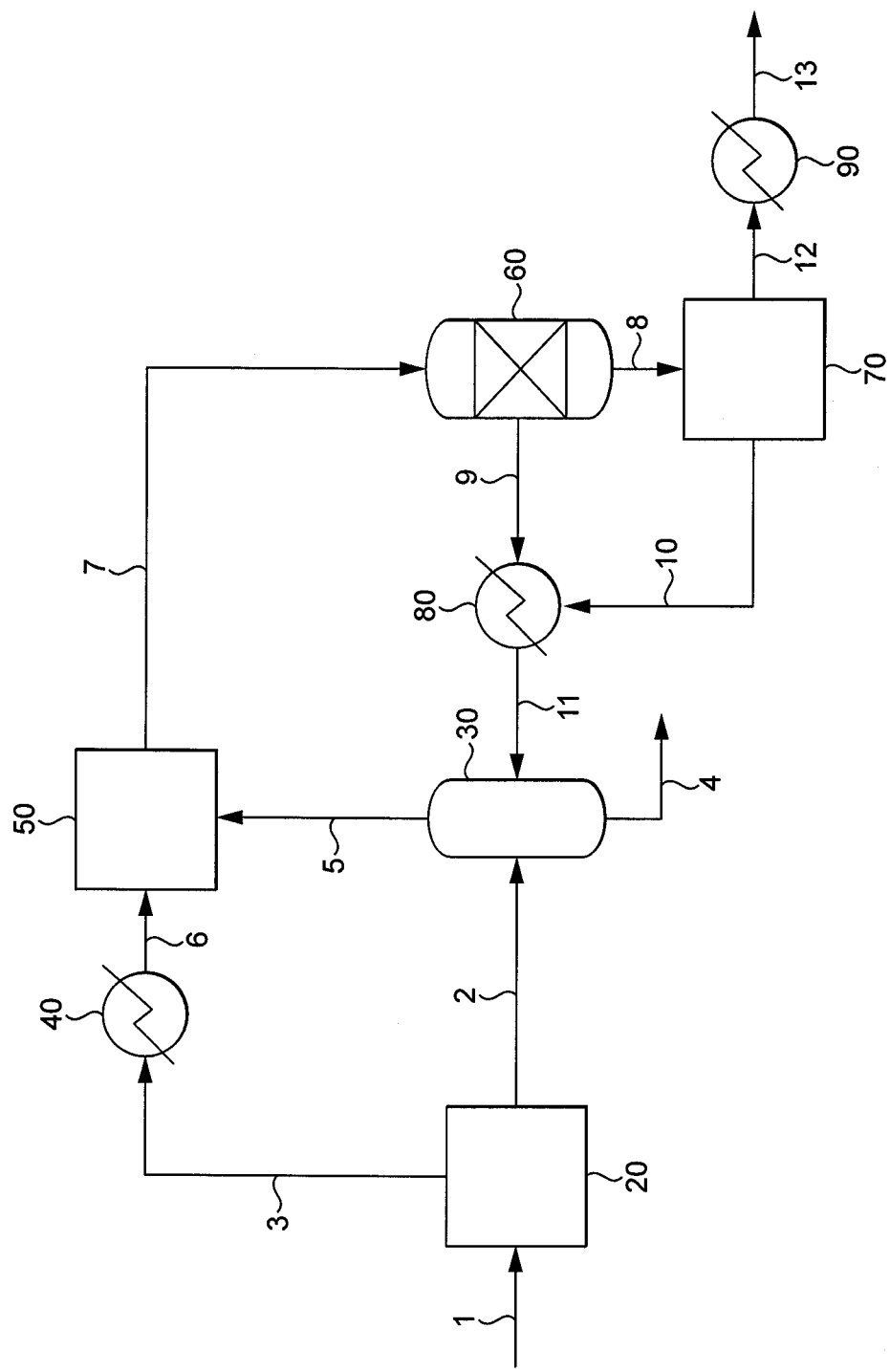

In one embodiment of the present invention, the, or each, drying unit comprises two or more parallel desiccant beds, wherein the vapour phase alcohol composition A and/or C is contacted with the desiccant bed in at least one of the desiccant beds (the 'active bed(s)') at the process temperature and pressure, whilst at least one of the other, parallel, desiccant beds is being regenerated (the 'regenerating bed(s)') by contacting a carrier fluid with the desiccant bed at an increased temperature relative to the active bed ("temperature swing adsorption"). In temperature swing adsorption systems operated in the gas phase, the pressure of both the active bed and the regenerating bed may be kept approximately constant. Advantageously, temperature swing adsorption systems may be operated entirely in the liquid phase. Operation of such systems would enable continuous regeneration of the desiccant beds through the use of systematic changing of the active and regenerating beds. Typical temperatures for regenerating the desiccant bed in temperature swing adsorption systems are temperatures having a minimum temperature of at least 180° C. and also being at least 10° C. greater than the process temperature; preferably, temperatures for regenerating the desiccant bed in temperature swing adsorption systems are temperatures having a minimum temperature of at least 200° C. and also being at least 15° C. greater than the process temperature; and, more preferably, temperatures for regenerating the desiccant bed in temperature swing adsorption systems are temperatures having a minimum temperature of at least at least 220° C. and also being at least 20° C. greater than the process temperature. By the term "process temperature", it is meant the temperature at which the vapour phase alcohol composition A and/or C is contacted with the desiccant bed (e.g. the temperature of the active bed). The heating of the desiccant bed in the regenerating bed may be achieved by preheating the carrier fluid prior to contacting it with the desiccant bed.

In one embodiment of the present invention, the, or each, drying unit comprises two or more parallel desiccant beds, wherein the vapour phase alcohol composition A and/or C is contacted with the desiccant bed in at least one of the desiccant beds (the 'active bed(s)') at the process temperature and pressure, whilst at least one of the other, parallel, desiccant beds is being regenerated (the 'regenerating bed(s)') by contacting a carrier gas with the desiccant bed at an decreased pressure relative to the active bed ("pressure swing adsorption"). In pressure swing adsorption systems, the temperature of both the active bed and the regenerating bed may be kept approximately constant. Operation of such systems would enable continuous regeneration of the desiccant beds through the use of systematic changing of the active and regenerating beds. Typical pressures for regenerating the desiccant bed in pressure swing adsorption systems are pressures having a maximum pressure of at most 0.2 MPa and also said pressure being at least 0.05 MPa lower than the process pressure; preferably, the pressures for regenerating the desiccant bed in pressure swing adsorption systems are pressures having a maximum pressure of at most 0.15 MPa and also said pressure being at least 0.075 MPa lower than the process pressure; and, more preferably, the pressures for regenerating the desiccant bed in pressure swing adsorption systems are pressures having a maximum pressure of at most 0.1 MPa and also said pressure being at least 0.1 MPa lower than the process pressure. By the term "process pressure", it is meant the pressure at which the vapour phase alcohol composition A and/or C is contacted with the desiccant bed (e.g. the pressure of the active bed). Systems which employ a combination of temperature swing adsorption and pressure swing adsorption may also be used in the process of the present invention.

The time required for the regeneration of the porous inorganic oxide material will be dependent upon the various factors, such as the amount of water adsorbed, the exact desiccant bed used, the temperature and/or pressure used during the regeneration cycle, the carrier fluid used during the regeneration cycle as well as the flow rate of the carrier fluid during the regeneration cycle. The time required for the regeneration of the desiccant bed can be readily determined through means known in the art, for example, it may be determined by monitoring the water content in the effluent carrier fluid during a regeneration cycle or by monitoring the temperature of the porous inorganic oxide material during a regeneration cycle.

The effluent alcohol composition from the process of the present invention has a reduced content of water and carboxylic acid relative to the alcohol composition which is fed to the process of the present invention.

In one aspect of the present invention, the alcohol composition which results from the process of the present invention has a water content and a carboxylic acid content which meets required specifications for fuel alcohol compositions. Thus, in one particular aspect of the present invention, the process of the present invention provides a method for reducing the water and carboxylic acid content of an alcohol composition which contains a water and/or carboxylic acid content which is greater than is permissible in a fuel alcohol specification, such that the water and/or carboxylic acid content of the alcohol composition is equal to or lower than the maximum water and/or carboxylic acid content required by the fuel alcohol specification.

In another particular aspect of the present invention, the process of the present invention provides a method for reducing the water and acetic acid content of an ethanol composition comprising ethanol, water and acetic acid, wherein said process comprises:

(a) forming a vapour phase ethanol composition A and a liquid phase ethanol composition B from the alcohol composition;

(b) separating a second vapour phase ethanol composition C and an aqueous phase D from the liquid phase ethanol composition B in a distillation column, wherein the aqueous phase D contains the majority of the acetic acid that was present in the liquid phase ethanol composition B;

(c) passing the vapour phase ethanol composition A to a drying unit comprising a desiccant;

(d) passing the vapour phase ethanol composition C to a drying unit comprising a desiccant; and (e) recovering an ethanol composition from the drying unit of step (c) and the drying unit of step (d);

wherein the recovered ethanol composition of step (e) has a reduced water and acetic acid content.

In another particular aspect of the present invention, the process of the present invention provides a method for the preparation of a fuel ethanol composition suitable for use in ethanol-containing gasoline compositions from an ethanol composition comprising ethanol, water and acetic acid, wherein said process comprises:

(a) forming a vapour phase ethanol composition A and a liquid phase ethanol composition B from the ethanol composition;

(b) separating a second vapour phase ethanol composition C and an aqueous phase D from the liquid phase ethanol composition B in a distillation column, wherein the aqueous phase D contains the majority of the acetic acid that was present in the liquid phase ethanol composition B;

(c) passing the vapour phase ethanol composition A to a drying unit comprising a desiccant;

(d) passing the vapour phase ethanol composition C to a drying unit comprising a desiccant; and (e) recovering a fuel ethanol composition from the drying unit of step (c) and the drying unit of step (d);

wherein the recovered fuel ethanol composition of step (e) has a reduced water and acetic acid content.

In another particular aspect of the present invention, the process of the present invention provides a method for reducing the water and butyric acid content of a butanol composition comprising at least one butanol, water and butyric acid, wherein said process comprises:

(a) forming a vapour phase butanol composition A and a liquid phase butanol composition B from the butanol composition;

(b) separating a second vapour phase butanol composition C and an aqueous phase
D from the liquid phase butanol composition B in a distillation column, wherein the aqueous phase D contains the majority of the butyric acid that was present in the liquid phase butanol composition B;

(c) passing the vapour phase butanol composition A to a drying unit comprising a desiccant;

(d) passing the vapour phase butanol composition C to a drying unit comprising a desiccant; and (e) recovering a butanol composition from the drying unit of step (c) and the drying unit of step (d);

wherein the recovered butanol composition of step (e) has a reduced water and butyric acid content.

In another particular aspect of the present invention, the process of the present invention provides a method for the preparation of a fuel butanol composition suitable for use in butanol-containing gasoline compositions from a butanol composition comprising at least one butanol, water and butyric acid, wherein said process comprises:

(a) forming a vapour phase butanol composition A and a liquid phase butanol composition B from the butanol composition;

(b) separating a second vapour phase butanol composition C and an aqueous phase D from the liquid phase butanol composition B in a distillation column, wherein the aqueous phase D contains the majority of the butyric acid that was present in the liquid phase butanol composition B;

(c) passing the vapour phase butanol composition A to a drying unit comprising a desiccant;

(d) passing the vapour phase butanol composition C to a drying unit comprising a desiccant; and (e) recovering a fuel butanol composition from the drying unit of step (c) and the drying unit of step (d);

wherein the recovered fuel butanol composition has a reduced water and butyric acid content.

In one specific aspect of the present invention, the alcohol composition which results from the process of the present invention is an ethanol composition having a water content and an acetic acid content which meets required specifications for fuel ethanol compositions.

The present invention further provides a system for reducing the water and carboxylic acid content of an alcohol composition comprising at least one alcohol having from one to four carbon atoms, water and at least one carboxylic acid having from one to four carbon atoms, wherein said system comprises:

(a) means to form a vapour phase alcohol composition A and a liquid phase alcohol composition B from the alcohol composition;

(b) a distillation column configured to separate a second vapour phase alcohol composition C and an aqueous phase D from the liquid phase alcohol composition B, wherein the aqueous phase D contains the majority of the carboxylic acid that was present in the liquid phase alcohol composition;

(c) a drying unit comprising a desiccant through which the vapour phase alcohol composition A is passed; and (d) a drying unit comprising a desiccant through which the vapour phase alcohol composition C is passed.

The system of the present invention comprises means to form a vapour phase alcohol composition A and a liquid phase alcohol composition B from the alcohol composition. The means to form the vapour phase alcohol composition A and the liquid phase alcohol composition B may be any suitable means for forming a vapour phase and a liquid phase from the alcohol composition.

In a first specific embodiment, the means to form the vapour phase alcohol composition A and the liquid phase alcohol composition B comprises a vaporisation unit configured to vaporise part of the alcohol composition to form the vapour phase alcohol composition A and the liquid phase alcohol composition B.

In an alternative embodiment, the means to form the vapour phase alcohol composition A and the liquid phase alcohol composition B comprises means to pre-divide the alcohol composition into a first portion and a second portion, and a vaporisation unit configured to vaporise substantially all of the first portion.

In a further alternative embodiment, the means to form the vapour phase alcohol composition A and the liquid phase alcohol composition B comprises means to pre-divide the alcohol composition into a first portion and a second portion, and a vaporisation unit configured to vaporise part of the first portion to form the vapour phase alcohol composition A and a third portion, the second portion and the third portion together forming liquid phase alcohol composition B. In this embodiment, the means to form the vapour phase alcohol composition A and the liquid phase alcohol composition B may further comprise means to pass the second portion and the third portion separately to the distillation column, or means to combine the second portion and the third portion before they are passed to the distillation column.

In the embodiment of the system of the present invention comprising means to pre-divide the alcohol composition into a first portion and a second portion, the means may comprise any suitable means for dividing an alcohol composition into two portions, preferably the two portions having the same composition, but optionally having different sizes, such as by flow control.

Vaporisation units suitable for use in the system of the present invention comprise any vaporisation units capable of fully vaporising and/or partially vaporising an alcohol composition comprising at least one alcohol having from one to four carbon atoms, water and at least one carboxylic acid having from one to four carbon atoms.

Distillation columns suitable for use in systems according to the present invention comprise any distillation columns suitable to separate the liquid phase alcohol composition B into a second vapour phase alcohol composition C and an aqueous phase D.

The system of the present invention comprises a drying unit comprising a desiccant through which the vapour phase alcohol composition A is passed, and a drying unit comprising a desiccant through which the vapour phase alcohol composition C is passed. These may be separate drying units; however, in a preferred embodiment, the drying unit through which the vapour phase alcohol composition C is passed is the same drying unit as the drying unit through which the vapour phase alcohol composition A is passed. In this embodiment, the system according to the present invention will comprise only a single drying unit.

The, or each, drying unit forming part of the system according to the present invention may comprise a single or multiple desiccant beds.

The present invention further comprises a method of preparing a fuel alcohol composition from an alcohol composition comprising at least one alcohol having from one to four carbon atoms, water and at least one carboxylic acid having from one to four carbon atoms, wherein said method involves:

(a) determining the concentration of water and carboxylic acid present in the alcohol composition;

(b) if the alcohol composition comprises a concentration of water which is greater than the azeotropic concentration for the alcohol composition, passing the entire alcohol composition to a distillation column of step (c) as a liquid phase alcohol composition B; if the alcohol composition comprises a concentration of water which is equal to or lower than the azeotropic concentration for the alcohol composition, and the carboxylic acid concentration is equal to or lower than the maximum desired concentration of carboxylic acid in the fuel alcohol composition, vaporising the entire alcohol composition to form a vapour phase alcohol composition A; or if the alcohol composition comprises a concentration of water which is equal to or lower than the azeotropic concentration for the alcohol composition, and the carboxylic acid concentration is greater than the maximum desired concentration of carboxylic acid in the fuel alcohol composition, forming a vapour phase alcohol composition A and a liquid phase alcohol composition B from the alcohol composition;

(c) separating a second vapour phase ethanol composition C and an aqueous phase D from the liquid phase ethanol composition B, if present, in a distillation column, wherein the aqueous phase D contains the majority of the carboxylic acid that was present in the liquid phase alcohol composition B;

(d) passing the vapour phase alcohol composition A, if present, to a drying unit comprising a desiccant;

(e) passing the vapour phase alcohol composition C, if present, to a drying unit comprising a desiccant; and (f) recovering a fuel alcohol composition from the drying unit of step (d), if present, and the drying unit of step (e), if present;

wherein the recovered fuel alcohol composition has a reduced water content.

In the method of preparing a fuel alcohol composition of the present invention, the step of determining the concentration of water and carboxylic acid present in the alcohol composition may be carried out in any conventional way.

Figure 2:
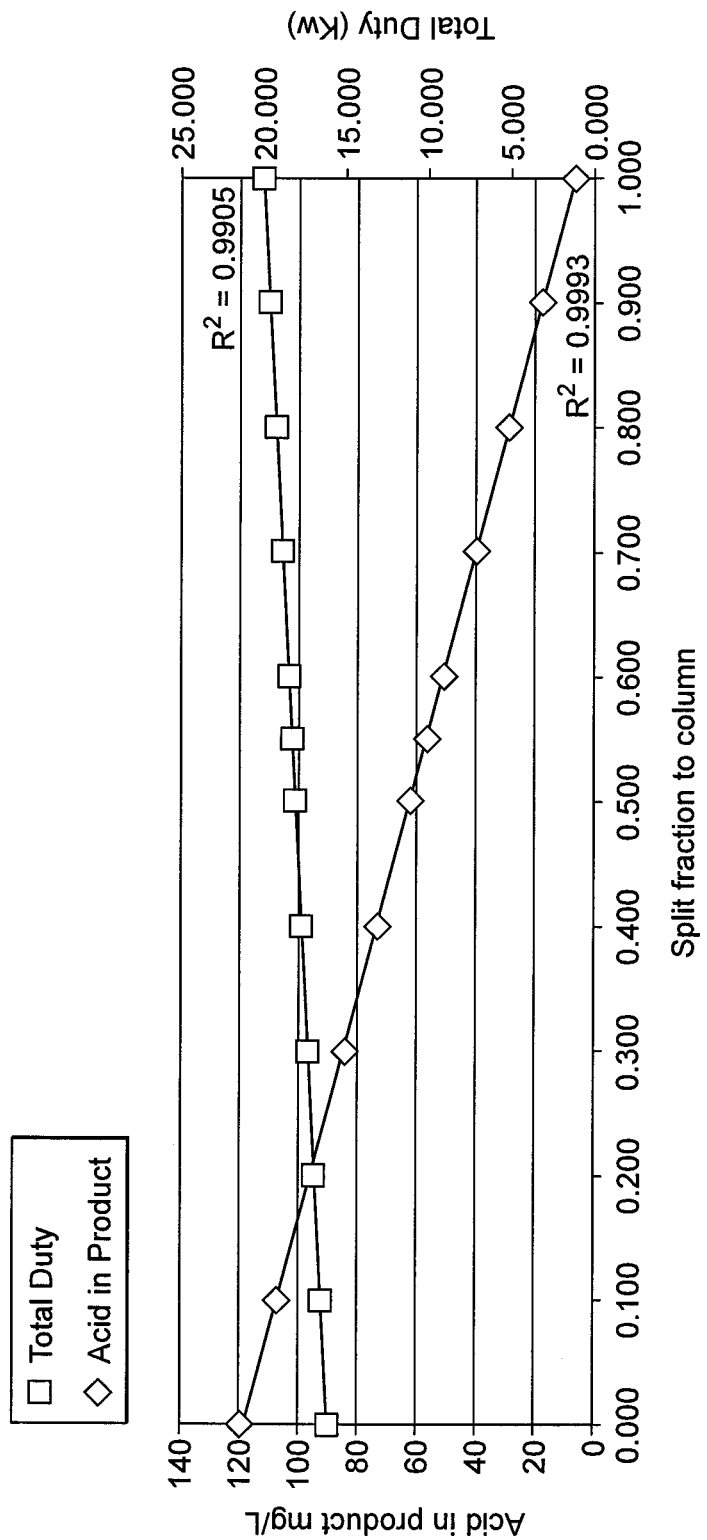
Figure 3:
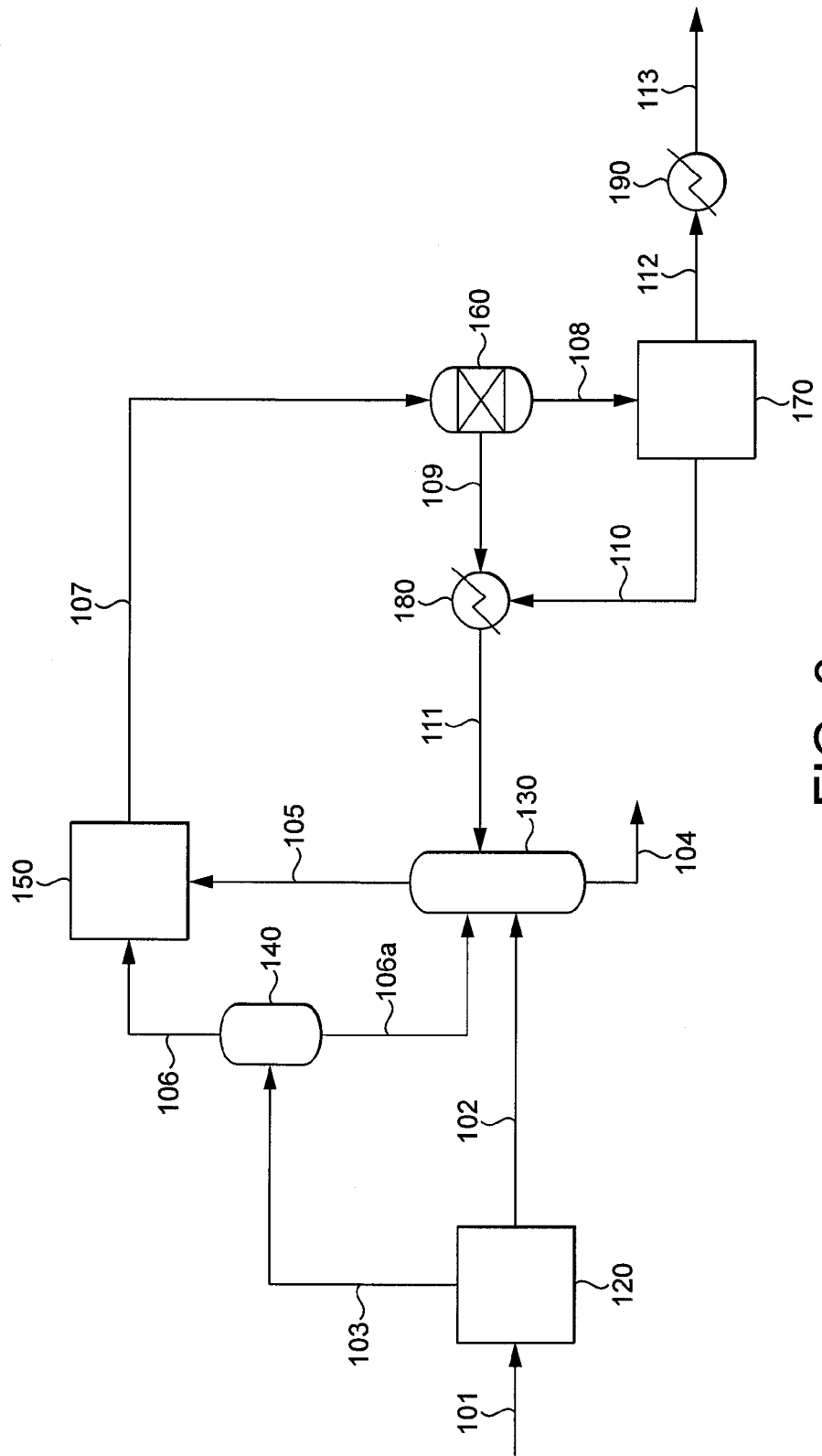
Figure 4:
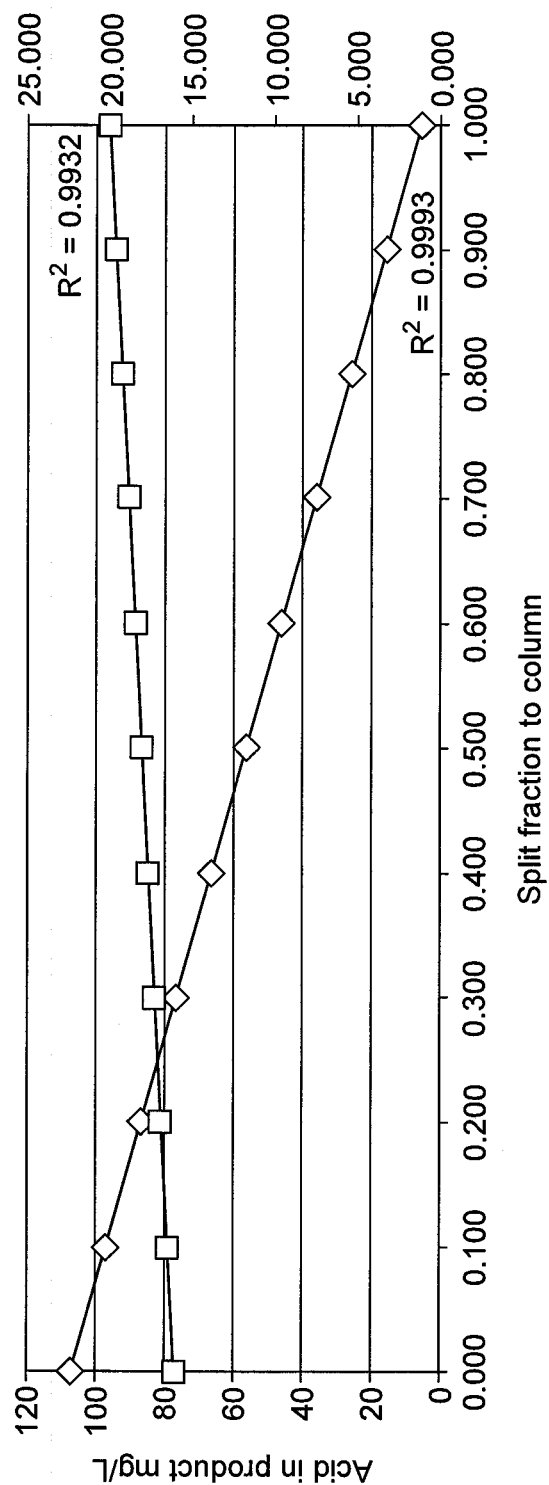
Figure 5:
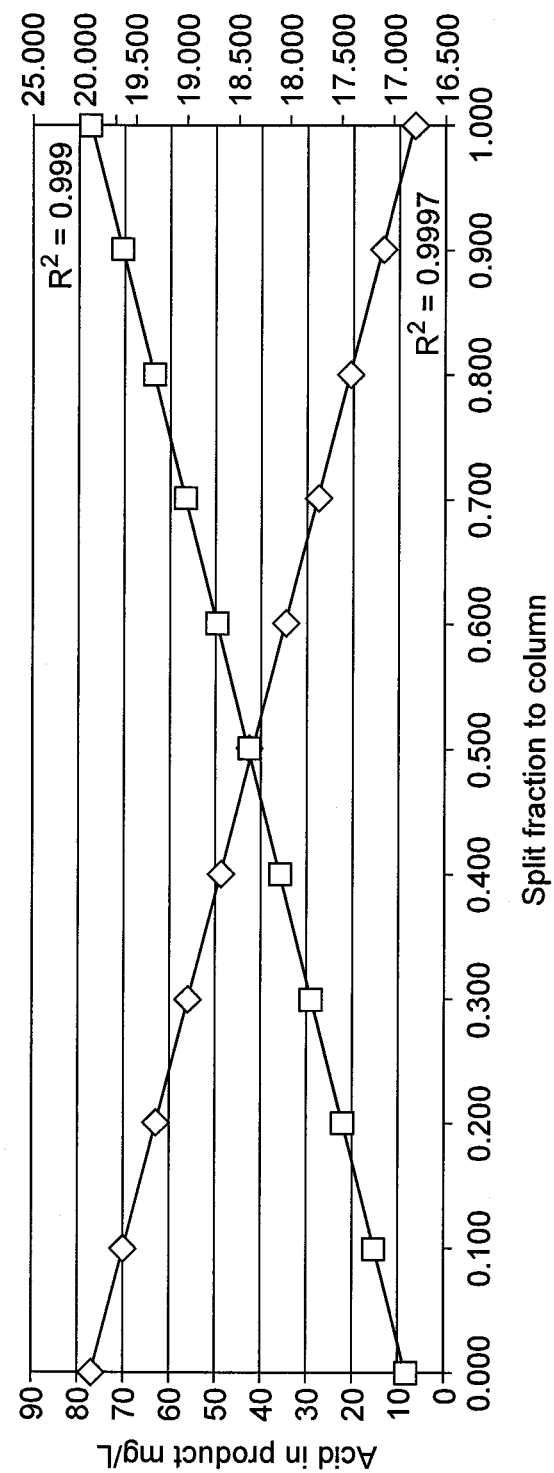

The present invention will now be illustrated, without limiting the scope thereof, with reference to the following Examples and the accompanying Figures in which:

FIG. 1 shows an embodiment of a process and apparatus of the present invention;

FIG. 2 provides a plot of acid in product (mg/L) and total duty versus split fraction, corresponding to the embodiment of FIG. 1;

FIG. 3 shows another embodiment of a process and apparatus of the present invention;

FIG. 4 provides a plot of acid in product (mg/L) and total duty versus split fraction, corresponding to the embodiment of FIG. 3 operated with a 1% blowdown from vaporizer (140); and FIG. 5 provides a further plot of acid in product (mg/L) and total duty versus split fraction, corresponding to the embodiment of FIG. 3 operated with a 5% blowdown from vaporizer (140);

DETAILED DESCRIPTION OF THE INVENTION

FIG. 1 shows an embodiment of a system and apparatus for reducing the water and carboxylic acid content of an alcohol composition in accordance with the present invention. The apparatus comprises a first splitter (20), a distillation column (30), a vaporiser (40), a mixer/heater (50), a drying unit (60) comprising a desiccant, for example molecular sieve 3A and/or molecular sieve 4A, a second splitter (70), a first cooler (80) and a second cooler (90).

An alcohol composition (1), comprising at least one alcohol having from one to four carbon atoms, water and at least one carboxylic acid having from one to four carbon atoms enters the process and is separated in the first splitter (20) into a first portion (3) and a second portion (2). The relative sizes of the first portion (3) and the second portion (2) are controlled by adjusting the splitter, and, advantageously, may be selected so that the acid level in the final product meets the appropriate specification. The first portion (3) is passed to the vaporiser (40), where it is heated so that substantially all of the first portion is converted into a first vapour phase alcohol composition (6). The second portion removed from the divider (20) is passed to the distillation column (30), where it is separated by distillation into a second vapour phase alcohol composition (5) and an aqueous phase (4). Optionally, the distillation column (30) receives an additional alcohol and water feed stream (11) obtained by regenerating the drying unit (60), and optionally further comprising part of the effluent (8) from the drying unit (60). The aqueous phase (4) contains a majority of the carboxylic acid that was present in the liquid phase alcohol composition (2), and also the majority of the carboxylic acid that was present in the additional water and alcohol feed stream (11), if present.

The first vapour phase alcohol composition (6) and the second vapour phase alcohol composition (5) are combined in the mixer/heater (50), and are heated therein, for example to 160° C., to form a combined vapour phase alcohol composition (7). The combined alcohol vapour phase (7) is passed to the drying unit (60), which comprises at least one desiccant bed, preferably comprising at least one porous inorganic oxide material containing Brønsted acid sites and/or neutralised Brønsted acid sites, such as molecular sieve 3A and/or molecular sieve 4A. Passing the combined vapour phase alcohol composition (7) through the dryer (60) removes a large portion of the water from the combined vapour phase alcohol composition, and an alcohol composition (8) having a reduced water and carboxylic acid content compared to the water and carboxylic acid content of the feed stream (1) is withdrawn from the drying unit (60).

Optionally, the alcohol composition having a reduced water and carboxylic acid content (8) is divided into a first portion (10) and a second portion (12) in the second splitter (70). The first portion (10) and the second portion (12) will have substantially the same compositions, but the size of each portion may be adjusted by adjustment of the splitter (70). The relative size of the first portion (10) and the second portion (12) will be selected to provide a suitable composition for the additional feed (11) to the distillation column (30).

Water removed from the combined vapour phase alcohol composition (7) in the drying unit (60) may be removed therefrom as a water stream (9), and this may be combined with the first portion (10) of the alcohol composition having a reduced water and carboxylic acid content (8) in the first cooler/condenser (80), where it is cooled to, for example, 50° C., to form an additional water and alcohol feed stream (11), which may be passed to the distillation column (30).

Alternatively or additionally, the first portion (10) of the alcohol composition having a reduced water and carboxylic acid composition (8) obtained in the second splitter (70) may be used to regenerate a desiccant bed in the dryer (60), and this will produce a mixture of water and alcohol which may be fed to the distillation unit (30) as the additional water and ethanol feed stream (11).

The second portion (12) of the alcohol composition having a reduced water and carboxylic acid content (8), which may represent substantially all of the alcohol composition having a reduced water and carboxylic acid content (8) recovered from the drying unit (60), may optionally be further cooled in second cooler (90), for example to 20° C., to form a cooled alcohol composition having a reduced water and carboxylic acid content (13). The cooled alcohol composition having a reduced water and carboxylic acid content (13) may be used as a fuel component or used for any other conventional use.

The distillation column (30) has 11 theoretical stages with no condenser, stage 11 being equivalent to a reboiler. Second portion (2) of the alcohol composition (1) enters the distillation column (30) above stage 1. The additional water and ethanol feed stream (11) enters the distillation column (30) above stage 5.

FIG. 3 shows another embodiment of a system and apparatus for reducing the water and carboxylic acid content of an alcohol composition in accordance with the present invention. The apparatus comprises a first splitter (120), a first distillation column (130), a second distillation column (140), a mixer/heater (150), a drying unit (160) comprising a desiccant, for example molecular sieve 3A and/or molecular sieve 4A, a second splitter (170), a first cooler (180) and a second cooler (190).

An alcohol composition (101), comprising at least one alcohol having from one to four carbon atoms, water and at least one carboxylic acid having from one to four carbon atoms enters the process and is separated in the first splitter (120) into a first portion (103) and a second portion (102).

The relative sizes of the first portion (103) and the second portion (102) are controlled by adjusting the splitter, and, advantageously, may be selected so that the acid level in the final product meets the appropriate specification. The first portion (103) is passed to the second distillation column (140), where it is separated by distillation so that substantially all of the first portion is separated into a first vapour phase alcohol composition (106) and a liquid base composition (106a). The second portion removed from the splitter (120) and the liquid base composition (106a) are passed to the first distillation column (130), where they are separated by distillation into a second vapour phase alcohol composition (105) and an aqueous phase (104). Optionally, the first distillation column (130) receives an additional alcohol and water feed stream (111) obtained by regenerating the drying unit (160), and optionally further comprising part of the effluent (108) from the drying unit (160). The aqueous phase (104) contains a majority of the carboxylic acid that was present in the liquid phase alcohol composition (102), and also the majority of the carboxylic acid that was present in the additional water and alcohol feed stream (111), if present.

The first vapour phase alcohol composition (106) and the second vapour phase alcohol composition (105) are combined in the mixer/heater (150), and are heated therein, for example to 160° C., to form a combined vapour phase alcohol composition (107). The combined alcohol vapour phase (107) is passed to the drying unit (160), which comprises at least one desiccant bed, preferably comprising at least one porous inorganic oxide material containing Brønsted acid sites and/or neutralised Brønsted acid sites, such as molecular sieve 3A and/or molecular sieve 4A. Passing the combined vapour phase alcohol composition (107) through the dryer (160) removes a large portion of the water from the combined vapour phase alcohol composition, and an alcohol composition (108) having a reduced water and carboxylic acid content compared to the water and carboxylic acid content of the feed stream (101) is withdrawn from the drying unit (160).

Optionally, the alcohol composition having a reduced water and carboxylic acid content (108) is divided into a first portion (110) and a second portion (112) in the second splitter (170). The first portion (110) and the second portion (112) will have substantially the same compositions, but the size of each portion may be adjusted by adjustment of the splitter (170). The relative size of the first portion (110) and the second portion (112) will be selected to provide a suitable composition for the additional feed (111) to the distillation column (130).

Water removed from the combined vapour phase alcohol composition (107) in the drying unit (160) may be removed therefrom as a water stream (109), and this may be combined with the first portion (110) of the alcohol composition having a reduced water and carboxylic acid content (108) in the first cooler/condenser (180), where it is cooled to, for example, 50° C., to form an additional water and alcohol feed stream (111), which may be passed to the distillation column (130).

Alternatively or additionally, the first portion (110) of the alcohol composition having a reduced water and carboxylic acid composition (108) obtained in the second splitter (170) may be used to regenerate a desiccant bed in the dryer (160), and this will produce a mixture of water and alcohol which may be fed to the distillation unit (130) as the additional water and ethanol feed stream (111).

The second portion (112) of the alcohol composition having a reduced water and carboxylic acid content (108), which may represent substantially all of the alcohol composition having a reduced water and carboxylic acid content (108) recovered from the drying unit (160), may optionally be further cooled in second cooler (190), for example to 20° C., to form a cooled alcohol composition having a reduced water and carboxylic acid content (113). The cooled alcohol composition having a reduced water and carboxylic acid content (113) may be used as a fuel component or used for any other conventional use.

The first distillation column (130) has 11 theoretical stages with no condenser, stage 11 being equivalent to a reboiler. Second portion (102) of the alcohol composition (101) enters the first distillation column (130) above stage 1. The additional water and ethanol feed stream (111) enters the first distillation column (130) above stage 5.

EXAMPLES

Example 1

An ethanol feedstock comprising 2% wt % water and 150 ppmw acetic acid (1.6 vol % water and 121 mg/L acetic acid) was used as the feed stream to a system as illustrated in FIG. 1. A process according to the present invention was carried out a number of times, with the feed stream being split into first and second portions of different sizes, as illustrated in Table 1, in different runs. Table 1 also lists reboiler duty of the distillation column (30), and heating duty of the vaporiser (40), plus total duty. The table also lists the amount of water in the product (as volume %), water removal and the acid remaining in the product (in mg/L).

The results in Table 1 for acid in product and total duty versus split fraction to the distillation column are shown graphically in FIG. 2.

TABLE 1

| Split to Colum 30 | Split to Evaporator 40 | Column Reboiler Duty (kW) | Evaporator Duty (kW) | Total Duty (kW) | Water in product (vol %) | Water removal | Acid in product (mg/L) |
|---|---|---|---|---|---|---|---|
| 0.000 | 1.000 | 0.461 | 15.307 | 15.768 | 0.80 | 0.596 | 120 |
| 0.100 | 0.900 | 2.739 | 13.776 | 16.515 | 0.80 | 0.743 | 108 |
| 0.200 | 0.800 | 4.736 | 12.245 | 16.981 | 0.80 | 0.790 | 96 |
| 0.300 | 0.700 | 6.670 | 10.715 | 17.385 | 0.80 | 0.818 | 84 |
| 0.400 | 0.600 | 8.584 | 9.184 | 17.768 | 0.80 | 0.839 | 73 |
| 0.500 | 0.500 | 10.486 | 7.653 | 18.140 | 0.80 | 0.854 | 62 |
| 0.550 | 0.450 | 11.440 | 6.888 | 18.328 | 0.80 | 0.861 | 56 |
| 0.600 | 0.400 | 12.389 | 6.123 | 18.512 | 0.80 | 0.867 | 51 |
| 0.700 | 0.300 | 14.273 | 4.592 | 18.865 | 0.80 | 0.877 | 40 |
| 0.800 | 0.200 | 16.164 | 3.061 | 19.225 | 0.80 | 0.886 | 29 |

TABLE 1-continued

| Split to Colum 30 | Split to Evaporator 40 | Column Reboiler Duty (kW) | Evaporator Duty (kW) | Total Duty (kW) | Water in product (vol %) | Water removal | Acid in product (mg/L) |
|---|---|---|---|---|---|---|---|
| 0.900 | 0.100 | 18.048 | 1.531 | 19.579 | 0.80 | 0.893 | 18 |
| 1.000 | 0.000 | 19.932 | 0.000 | 19.932 | 0.80 | 0.899 | 8 |

As illustrated in FIG. 2, increasing the proportion of the feed stream divided to the distillation column increases the total energy duty for running the process, but results in a decrease in the amount of acid in the final product. Thus, selecting the proportion of the feed divided to the distillation column, and the portion divided to the vaporisation unit, allows one to minimise the total duty of the system for a given acid content in the final product; i.e., it is possible to minimise the power required for a given acid level required to satisfy a particular alcohol fuel specification.

The compositions of the feed stream and the various streams produced in the process when the feed stream was split to feed 55% to the distillation column (30) and 45% to the evaporator (40) are shown in Table 2, using numbering corresponding to that employed in FIG. 1.

TABLE 2

| STREAM | 1 | 2 | 3 | 4 | 5 | 6 |
|---|---|---|---|---|---|---|
| MASS FLOW | | | | | | |
| Acetic acid, kg/hr | 7.5 | 4.1 | 3.4 | 4.1 | 0.3 | 3.4 |
| Water, kg/hr | 1000.0 | 550.0 | 450.0 | 509.4 | 3311.8 | 450.0 |
| Ethanol, kg/hr | 48992.5 | 26945.9 | 22046.6 | 0.3 | 30216.8 | 22046.6 |
| VOL. FRAC. (LIQUID) | | | | | | |
| Water, vol % | 1.6% | 1.6% | 1.6% | 99.1% | | |
| Ethanol, vol % | 98.4% | 98.4% | 98.4% | 0.1% | | |
| MASS CONC. (LIQUID) | | | | | | |
| Acetic acid, mg/L | 121 | 121 | 121 | 6790 | | |

| STREAM | 7 | 8 | 9 | 10 | 11 | 12 |
|---|---|---|---|---|---|---|
| MASS FLOW | | | | | | |
| Acetic acid, kg/hr | 3.7 | 3.7 | 0.0 | 0.2 | 0.2 | 3.4 |
| Water, kg/hr | 3761.8 | 523.3 | 3238.5 | 32.8 | 3271.2 | 490.6 |
| Ethanol, kg/hr | 52263.5 | 52263.5 | 0.0 | 3271.2 | 3271.2 | 48992.3 |
| VOL. FRAC. (LIQUID) | | | | | | |
| Water, vol % | | | | | 44.8% | |
| Ethanol, vol % | | | | | 55.6% | |
| MASS CONC. (LIQUID) | | | | | | |
| Acetic acid, mg/L | | | | | 31 | |

| STREAM | 13 |
|---|---|
| MASS FLOW | |
| Acetic acid, kg/hr | 3.4 |
| Water, kg/hr | 490.6 |
| Ethanol, kg/hr | 48992.3 |
| VOL. FRAC. (LIQUID) | |
| Water, vol % | 0.8% |
| Ethanol, vol % | 99.2% |
| MASS CONC. (LIQUID) | |
| Acetic acid, mg/L | 56 |

The water content of the final product is 0.8 volume %, and the acetic acid composition is 56 mg/L, both of which satisfy various specifications for denatured fuel ethanol, such as China Specification GB 18350-2001.

Example 2

An ethanol feedstock comprising 2% wt % water and 150 ppmw acetic acid (1.6 vol % water and 121 mg/L acetic acid) was used as the feed stream to a system as illustrated in FIG. 3. A process according to the present invention was carried out a number of times, with the feed stream being split into first and second portions of different sizes, as illustrated in Tables 3-4, in different runs. Tables 3 and 4 also list reboiler duty of the first distillation column (130), and heating duty of the vaporiser (140), plus total duty. The tables also list the amount of water in the product (as volume %), water removal and the acid remaining in the product (in mg/L). Table 3 corresponds to a 1% blowdown from vaporizer (140) and Table 4 corresponds to a 5% blowdown from vaporizer (140).

The results in Tables 3 and 4 for acid in product and total duty versus split fraction to the distillation column are shown graphically in FIGS. 4 and 5 respectively.

TABLE 3

| Split to Column 130 | Split to Evaporator 140 | Column 130 Reboiler Duty (kW) | Evaporator 140 Duty (kW) | Total Duty (kW) | Water in product (vol %) | Water removal | Acid in product (mg/L) |
|---|---|---|---|---|---|---|---|
| 0.000 | 1.000 | 0.793 | 15.197 | 15.990 | 0.80 | 0.573 | 110 |
| 0.100 | 0.900 | 2.963 | 13.677 | 16.640 | 0.80 | 0.758 | 98 |
| 0.200 | 0.800 | 4.926 | 12.158 | 17.084 | 0.80 | 0.798 | 87 |
| 0.300 | 0.700 | 6.834 | 10.638 | 17.472 | 0.80 | 0.823 | 77 |
| 0.400 | 0.600 | 8.726 | 9.118 | 17.844 | 0.80 | 0.842 | 66 |
| 0.500 | 0.500 | 10.609 | 7.598 | 18.207 | 0.80 | 0.857 | 56 |
| 0.600 | 0.400 | 12.474 | 6.079 | 18.552 | 0.80 | 0.868 | 46 |

TABLE 3-continued

| Split to Column 130 | Split to Evaporator 140 | Column 130 Reboiler Duty (kW) | Evaporator 140 Duty (kW) | Total Duty (kW) | Water in product (vol %) | Water removal | Acid in product (mg/L) |
|---|---|---|---|---|---|---|---|
| 0.700 | 0.300 | 14.340 | 4.559 | 18.899 | 0.80 | 0.878 | 37 |
| 0.800 | 0.200 | 16.208 | 3.039 | 19.247 | 0.80 | 0.886 | 27 |
| 0.900 | 0.100 | 18.071 | 1.520 | 19.591 | 0.80 | 0.893 | 17 |
| 1.000 | 0.000 | 19.932 | 0.000 | 19.932 | 0.80 | 0.899 | 8 |

TABLE 4

| Split to Column 130 | Split to Evaporator 140 | Column 130 Reboiler Duty (kW) | Evaporator 140 Duty (kW) | Total Duty (kW) | Water in product (vol %) | Water removal | Acid in product (mg/L) |
|---|---|---|---|---|---|---|---|
| 0.000 | 1.000 | 2.050 | 14.758 | 16.808 | 0.80 | 0.774 | 78 |
| 0.100 | 0.900 | 3.908 | 13.282 | 17.191 | 0.80 | 0.806 | 71 |
| 0.200 | 0.800 | 5.715 | 11.806 | 17.522 | 0.80 | 0.826 | 63 |
| 0.300 | 0.700 | 7.510 | 10.331 | 17.841 | 0.80 | 0.842 | 56 |
| 0.400 | 0.600 | 9.289 | 8.855 | 18.143 | 0.80 | 0.854 | 49 |
| 0.500 | 0.500 | 11.066 | 7.379 | 18.445 | 0.80 | 0.865 | 42 |
| 0.600 | 0.400 | 12.840 | 5.903 | 18.743 | 0.80 | 0.874 | 35 |
| 0.700 | 0.300 | 14.616 | 4.427 | 19.044 | 0.80 | 0.881 | 28 |
| 0.800 | 0.200 | 16.390 | 2.952 | 19.341 | 0.80 | 0.888 | 21 |
| 0.900 | 0.100 | 18.161 | 1.476 | 19.637 | 0.80 | 0.894 | 14 |
| 1.000 | 0.000 | 19.932 | 0.000 | 19.932 | 0.80 | 0.899 | 8 |

As illustrated in FIGS. 4-5, increasing the proportion of the feed stream divided to the distillation column increases the total energy duty for running the process, but results in a decrease in the amount of acid in the final product. Thus, selecting the proportion of the feed divided to the distillation column, and the portion divided to the vaporisation unit, allows one to minimise the total duty of the system for a given acid content in the final product; i.e., it is possible to minimise the power required for a given acid level required to satisfy a particular alcohol fuel specification.

The compositions of the feed stream and the various streams produced in the process corresponding to FIG. 3 and Table 3, when the feed stream was split to feed 50% to the first distillation column (130) and 50% to the second distillation column (140) are shown in Table 5, using numbering corresponding to that employed in FIG. 3. Commensurately, the compositions of the feed stream and the various streams produced in the process corresponding to FIG. 3 and Table 4, when the feed stream was split to feed 30% to the first distillation column (130) and 70% to the second distillation column (140) are shown in Table 6, also using numbering corresponding to that employed in FIG. 3.

TABLE 5

| STREAM | 101 | 102 | 103 | 104 | 105 | 106 |
|---|---|---|---|---|---|---|
| MASS FLOW | | | | | | |
| Acetic acid, kg/hr | 7.5 | 3.8 | 3.8 | 4.0 | 0.3 | 0.3 |
| Water, kg/hr | 1000.0 | 500.0 | 500.0 | 509.5 | 3147.3 | 5.0 |
| Ethanol, kg/hr | 48992.5 | 24496.3 | 24496.3 | 0.3 | 27892.8 | 244.9 |
| VOL. FRAC. (LIQUID) | | | | | | |
| Water, vol % | 1.6% | 1.6% | 1.6% | 99.1% | | 1.5% |
| Ethanol, vol % | 98.4% | 98.4% | 98.4% | 0.1% | | 98.4% |

TABLE 5-continued

| | | | | | | |
|---|---|---|---|---|---|---|
| MASS CONC. (LIQUID) | | | | | | |
| Acetic acid, mg/L | 121 | 121 | 121 | 6758 | | 910 |
| STREAM | 106a | 107 | 108 | 109 | 110 | 111 |
| MASS FLOW | | | | | | |
| Acetic acid, kg/hr | 3.4 | 3.7 | 3.7 | 0.0 | 0.2 | 0.2 |
| Water, kg/hr | 495.0 | 3642.4 | 522.1 | 3120.3 | 31.6 | 3151.9 |
| Ethanol, kg/hr | 24251.4 | 52144.2 | 52144.2 | 0.0 | 3151.8 | 3151.9 |
| VOL. FRAC. (LIQUID) | | | | | | |
| Water, vol % | | | | | | 44.8% |
| Ethanol, vol % | | | | | | 55.6% |
| MASS CONC. (LIQUID) | | | | | | |
| Acetic acid, mg/L | | | | | | 32 |
| STREAM | 112 | | | 113 | | |
| MASS FLOW | | | | | | |
| Acetic acid, kg/hr | 3.5 | | | 3.5 | | |
| Water, kg/hr | 490.5 | | | 490.5 | | |
| Ethanol, kg/hr | 48992.3 | | | 48992.3 | | |
| VOL. FRAC. (LIQUID) | | | | | | |
| Water, vol % | | | | 0.8% | | |
| Ethanol, vol % | | | | 99.2% | | |
| MASS CONC. (LIQUID) | | | | | | |
| Acetic acid, mg/L | | | | 56 | | |

TABLE 6

| STREAM | 101 | 102 | 103 | 104 | 105 | 106 |
|---|---|---|---|---|---|---|
| MASS FLOW | | | | | | |
| Acetic acid, kg/hr | 7.5 | 2.3 | 5.3 | 4.1 | 0.2 | 1.8 |
| Water, kg/hr | 1000.0 | 300.0 | 700.0 | 509.8 | 2613.8 | 34.7 |
| Ethanol, kg/hr | 48992.5 | 14697.8 | 34294.8 | 0.3 | 19200.8 | 1714.4 |
| VOL. FRAC. (LIQUID) | | | | | | |
| Water, vol % | 1.6% | 1.6% | 1.6% | 99.1% | | 1.5% |
| Ethanol, vol % | 98.4% | 98.4% | 98.4% | 0.1% | | 98.5% |
| MASS CONC. (LIQUID) | | | | | | |
| Acetic acid, mg/L | 121 | 121 | 121 | 6795 | | 687 |

| STREAM | 106a | 107 | 108 | 109 | 110 | 111 |
|---|---|---|---|---|---|---|
| MASS FLOW | | | | | | |
| Acetic acid, kg/hr | 3.5 | 3.6 | 3.6 | 0.0 | 0.2 | 0.2 |
| Water, kg/hr | 665.3 | 3279.2 | 518.4 | 2760.7 | 27.9 | 2788.9 |
| Ethanol, kg/hr | 32580.4 | 51781.2 | 51781.2 | 0.0 | 2788.7 | 2788.9 |
| VOL. FRAC. (LIQUID) | | | | | | |
| Water, vol % | | | | | | 44.8% |
| Ethanol, vol % | | | | | | 55.6% |
| MASS CONC. (LIQUID) | | | | | | |
| Acetic acid, mg/L | | | | | | 31 |

| STREAM | 112 | 113 |
|---|---|---|
| MASS FLOW | | |
| Acetic acid, kg/hr | 3.4 | 3.4 |
| Water, kg/hr | 490.5 | 490.5 |
| Ethanol, kg/hr | 48992.5 | 48992.5 |
| VOL. FRAC. (LIQUID) | | |
| Water, vol % | | 0.8% |
| Ethanol, vol % | | 99.2% |
| MASS CONC. (LIQUID) | | |
| Acetic acid, mg/L | | 56 |

The water content of the final product in both cases is 0.8 volume %, and the acetic acid composition is 56 mg/L, both of which satisfy various specifications for denatured fuel ethanol, such as China Specification GB 18350-2001.

The invention claimed is:

1. A process for reducing the water and carboxylic acid content of an alcohol composition comprising at least one alcohol having from one to four carbon atoms, water and at least one carboxylic acid having from one to four carbon atoms, wherein said process comprises:
   (a) forming a vapour phase alcohol composition A and a liquid phase alcohol composition B from the alcohol composition;
   (b) separating a second vapour phase alcohol composition C and an aqueous phase D from the liquid phase alcohol composition B in a distillation column, wherein the aqueous phase D contains the majority of the carboxylic acid that was present in the liquid phase alcohol composition B;
   (c) passing the vapour phase alcohol composition A to a drying unit comprising a desiccant;
   (d) passing the vapour phase alcohol composition C to a drying unit comprising a desiccant; and
   (e) recovering an alcohol composition from the drying unit of step (c) and the drying unit of step (d);
   wherein the recovered alcohol composition of step (e) has a reduced water and carboxylic acid content.

2. A process as claimed in claim 1, wherein the vapour phase alcohol composition A and the liquid phase alcohol composition B are formed by vaporisation of the alcohol composition.

3. A process as claimed in claim 1, wherein the vapour phase alcohol composition A and liquid phase alcohol composition B are formed by pre-dividing the alcohol composition into a first portion and a second portion, passing the first portion to a vaporisation unit so that substantially all of the first portion is vaporised in the vaporisation unit to form the vapour phase alcohol composition A, and passing the second portion to the distillation column as the liquid phase alcohol composition B.

4. A process as claimed in claim 1, wherein the vapour phase alcohol composition A and liquid phase alcohol composition B are formed by pre-dividing the alcohol composition into a first portion and a second portion, passing the first portion to a vaporisation unit so that the first portion is divided in the vaporisation unit into the vapour phase alcohol composition A and a third portion, and passing the second portion and the third portion to the distillation column as the liquid phase alcohol composition B.

5. A process as claimed in claim 1, wherein the vaporisation step does not result in a significant difference in the concentration of water present in the vapour phase alcohol composition A and the liquid phase alcohol composition B.

6. A process as claimed in claim 1, wherein the vapour phase alcohol composition A and the vapour phase alcohol composition C are passed to the same drying unit comprising a desiccant.

7. A process as claimed in claim 6, wherein the vapour phase alcohol composition A and the vapour phase alcohol composition C are combined prior to being passed to the drying unit comprising a desiccant.

8. A process as claimed in claim 1, wherein the alcohol composition comprises ethanol.

9. A process as claimed in claim 1, wherein the alcohol composition comprises acetic acid.

10. A process as claimed in claim 1, wherein the alcohol composition comprises at least one butanol.

11. A process as claimed in claim 1, wherein the alcohol composition comprises butyric acid.

12. A process as claimed in claim 1, wherein the alcohol composition has a water concentration in the range of from 0.05 wt % to 10 wt %.

13. A process as claimed in claim 1, wherein the alcohol composition has a carboxylic acid concentration in the range of 500 ppmw to 5 wt %.

14. A process as claimed in claim 1, further comprising using a portion of the alcohol composition having a reduced water and carboxylic acid content recovered in step (e) to regenerate the drying unit of step (c) and/or step (d), and optionally passing a portion of the resulting stream comprising alcohol and water to the distillation column.

15. A method of preparing a fuel alcohol composition from an alcohol composition comprising at least one alcohol having from one to four carbon atoms, water and at least one carboxylic acid having from one to four carbon atoms, wherein said method involves:
   (a) determining the concentration of water and carboxylic acid present in the alcohol composition;
   (b) if the alcohol composition comprises a concentration of water which is greater than the azeotropic concentration for the alcohol composition, passing the entire alcohol composition to a distillation column of step (c) as a liquid phase alcohol composition B;

if the alcohol composition comprises a concentration of water which is equal to or lower than the azeotropic concentration for the alcohol composition, and the carboxylic acid concentration is equal to or lower than the maximum desired concentration of carboxylic acid in the fuel alcohol composition, vaporising the entire alcohol composition to form a vapour phase alcohol composition A; or if the alcohol composition comprises a concentration of water which is equal to or lower than the azeotropic concentration for the alcohol composition, and the carboxylic acid concentration is greater than the maximum desired concentration of carboxylic acid in the fuel alcohol composition, forming a vapour phase alcohol composition A and a liquid phase alcohol composition B from the alcohol composition;

(c) separating a second vapour phase ethanol composition C and an aqueous phase D from the liquid phase ethanol composition B, if present, in a distillation column, wherein the aqueous phase D contains the majority of the carboxylic acid that was present in the liquid phase alcohol composition B;

(d) passing the vapour phase alcohol composition A, if present, to a drying unit comprising a desiccant;

(e) passing the vapour phase alcohol composition C, if present, to a drying unit comprising a desiccant; and (f) recovering a fuel alcohol composition from the drying unit of step (d), if present, and the drying unit of step (e), if present;

wherein the recovered fuel alcohol composition has a reduced water content.

* * * * *